United States Patent

Buret et al.

[11] 4,067,988
[45] Jan. 10, 1978

[54] 3-PHENYL-1,2,4-OXADIAZOLE DERIVATIVES AS ANTIINFLAMMATORY-ANTITUSSIVE AGENTS

[75] Inventors: Jean-Pierre Buret, Osny; Bernard Hercelin, Clermont; Jean-François Hamon, Saint-Ouen L'Aumone; Trajan Balea, Paris, all of France

[73] Assignee: Laboratoires Cassenne, Paris, France

[21] Appl. No.: 674,754

[22] Filed: Apr. 8, 1976

[30] Foreign Application Priority Data

Apr. 16, 1975 France .................. 75.11785

[51] Int. Cl.² .................. A61K 31/42; C07D 271/06
[52] U.S. Cl. .................. 424/272; 260/307 G
[58] Field of Search .................. 260/307 G; 424/272

[56] References Cited

U.S. PATENT DOCUMENTS

| | | | |
|---|---|---|---|
| 3,270,028 | 8/1966 | Palazzo | 260/307 |
| 3,879,407 | 4/1975 | Hagarty | 260/302 D |
| 3,887,573 | 6/1975 | Breuer et al. | 260/307 G |

*Primary Examiner*—Raymond V. Rush
*Attorney, Agent, or Firm*—Hammond & Littell

[57] ABSTRACT

3-Phenyl-1,2,4-oxadiazole derivatives of the formula

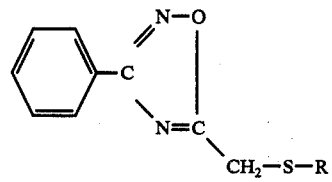

I wherein R is selected from the group consisting of
—$(CH_2)_m$—$COR_1$,

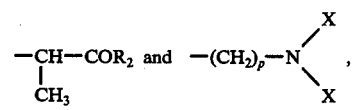

$m$ is 2, 3 or 4, $R_1$ is selected from the group consisting of hydroxy, alkoxy of 1 to 4 carbon atoms and

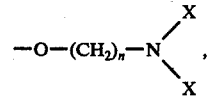

$n$ is 1 or 2, X is selected from the group consisting of hydrogen and alkyl of 1 to 4 carbon atoms, $R_2$ is selected from the group consisting of hydroxy, alkoxy of 1 to 4 carbon atoms,

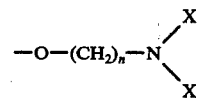

and —NH—$(CH_2)_n$—$COR_1$ and $p$ is 1, 2, 3 or 4 and the non-toxic, pharmaceutically acceptable salts thereof which have respiratory anti-inflammatory and peripheric antitussive properties and their preparation.

23 Claims, No Drawings

3-PHENYL-1,2,4-OXADIAZOLE DERIVATIVES AS ANTIINFLAMMATORY-ANTITUSSIVE AGENTS

STATE OF THE ART

French Pat. No. 2,213,054 describes oxadiazole derivatives of cephalosporin compounds as antibiotics but they are not related to the compounds of formula I.

OBJECTS OF THE INVENTION

It is an object of the invention to provide the novel oxadiazole derivatives of formula I and the salts thereof and a process for their preparation.

It is another object of the invention to provide novel antitussive and respiratory anti-inflammatory compositions and to a novel method for inducing respiratory anti-inflammatory and peripheric antitussive activity in warm-blooded animals, including humans.

These and other objects and advantages of the invention will become obvious from the following detailed description.

THE INVENTION

The novel 3-phenyl-1,2,4-oxadiazoles of the invention are selected from the group consisting of compounds of the formula

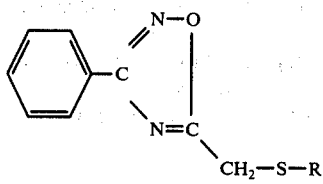
                                                                I wherein R is selected from the group consisting of —$(CH_2)_m$—$COR_1$,

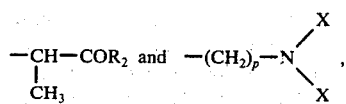

$m$ is 2,3 or 4, $R_1$ is selected from the group consisting of hydroxy, alkoxy of 1 to 4 carbon atoms and

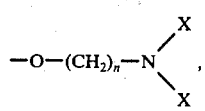

$n$ is 1 or 2, X is selected from the group consisting of hydrogen and alkyl of 1 to 4 carbon atoms, $R_2$ is selected from the group consisting of hydroxy, alkoxy of 1 to 4 carbon atoms,

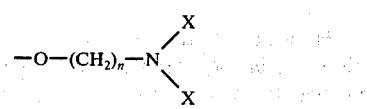

and —NH—$(CH_2)_n$—$COR_1$ and $p$ is 1,2,3 or 4 and the non-toxic, pharmaceutically acceptable salts thereof.

Examples of suitable alkoxy of 1 to 4 carbon atoms are methoxy, ethoxy or propoxy and examples of alkyl of 1 to 4 carbon atoms are methyl, ethyl, propyl, isopropyl and butyl.

The compounds of formula I wherein $R_1$ is other than hydroxy are basic in character and will form acid addition salts with a non-toxic, pharmaceutically acceptable acid such as inorganic acids like hydrochloric acid, hydrobromic acid, nitric acid, sulfuric acid or phorphoric acid or organic acids such as acetic acid, formic acid, benzoic acid, maleic acid, fumaric acid, succinic acid, tartric acid, citric acid, oxalic acid, benzylic acid, glyoxylic acid, asparatic acid, alkane sulfonic acids and arylsulfonic acids.

The compounds of formula I wherein $R_1$ is hydroxy are acidic in character and will form non-toxic, pharmaceutically acceptable salts of metals or nitrogen bases. Examples of suitable metals are alkali metals like sodium, potassium or lithium, alkaline earth metals such as calcium or metals such as aluminum or magnesium. Examples of nitrogen bases are ammonia and amines such as lysine, arginine or triethanolamine.

Among the preferred compounds of formula I are those wherein R is

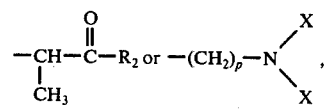

especially the former. Examples of specific compounds are 3-[S-(3-phenyl-1,2,4-oxadiazol-5-yl)-methyl]-thiopropionic acid and its alkyl esters of 1 to 4 carbon atoms; 2-[S-(3-phenyl-1,2,4-oxadiazol-5-yl)-methyl]-thiopropionic acid and its alkyl esters of 1 to 4 carbon atoms; 2-[S-(3-phenyl-1,2,4-oxadiazol-5-yl)-methyl]-thiopropionylglycine and its alkyl esters of 1 to 4 carbon atoms; particularly the ethyl ester and 2-[S-(3-phenyl-1,2,4-oxadiazol-5-yl)-methyl]-dimethylaminoethanethiol and its non-toxic, pharmaceutically acceptable acid addition salts, particularly its hydrochloride.

The novel process of the invention for the preparation of the compounds of formula I comprises reacting a compound of the formula

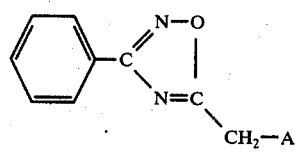
                                                                II wherein A is selected from the group consisting of chlorine, bromine, iodine and mercapto with a compound of the formula

B—R'     III wherein B is selected from the group consisting of chlorine, bromine, iodine and mercapto with the proviso that when B is mercapto, A is a halogen and when B is halogen, A is mercapto and R' is selected from the group consisting of

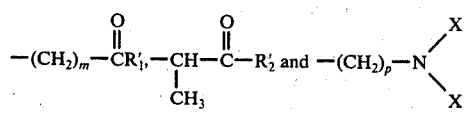

wherein $R_1'$ is alkoxy of 1 to 3 carbon atoms, $R_2'$ is alkoxy of 1 to 3 carbon atoms or —NH—$(CH_2)_n$—$COR_1'$ and $m$, $n$, $p$ and X have the above definitions to form a compound of the formula $$\underset{\underset{CH_2-S-R'}{|}}{\overset{N-O}{\underset{N=C}{C}}}\quad \text{Ia}$$

wherein R' has the above definition which may be isolated per se or be salified with an organic or inorganic acid.

When R' of formula Ia is $$-(CH_2)_m-\overset{O}{\overset{\|}{C}}R'_1 \text{ or } -\underset{\underset{CH_3}{|}}{CH}-\overset{O}{\overset{\|}{C}}-R'_2,$$

the compound may be saponified to obtain a compound of the formula $$\underset{\underset{CH_2-S-R''}{|}}{\overset{N-O}{\underset{N=C}{C}}}\quad \text{Ib}$$

wherein R'' is $-(CH_2)_m-COOH$, $$-\underset{\underset{CH_3}{|}}{CH}-\overset{O}{\overset{\|}{C}}-OH \text{ or } -\underset{\underset{CH_3}{|}}{CH}-\overset{O}{\overset{\|}{C}}-NH-(CH_2)_n-COOH$$

which may be isolated per se or salified with an organic or inorganic acid or esterified with an alkanol of 1 to 4 carbon atoms to obtain a compound of the formula $$\underset{\underset{CH_2-S-R'''}{|}}{\overset{N-O}{\underset{N=C}{C}}}\quad \text{Ic}$$

wherein R''' is $-(CH_2)_m-COR_1''$, $$-\underset{\underset{CH_3}{|}}{CH}-\overset{O}{\overset{\|}{C}}-R_1'' \text{ or } -\underset{\underset{CH_3}{|}}{CH}-\overset{O}{\overset{\|}{C}}-NH-(CH_2)_n-\overset{O}{\overset{\|}{C}}R_1''$$

wherein $R_1''$ is alkoxy of 1 to 4 carbon atoms or esterified with an amino alcohol of the formula $$HO-(CH_2)_n-N\underset{X}{\overset{X}{<}} \quad \text{IV}$$

to obtain a compound of formula Ic wherein R''' is $$-(CH_2)_m-\overset{O}{\overset{\|}{C}}-R_1'', -\underset{\underset{CH_3}{|}}{CH}-\overset{O}{\overset{\|}{C}}-R_1'' \text{ or}$$

-continued $$-\underset{\underset{CH_3}{|}}{CH}-\overset{O}{\overset{\|}{C}}NH-(CH_2)_n-COR_1''$$

wherein $R_1''$ is $$-O-(CH_2)_n-N\underset{X}{\overset{X}{<}}$$

which may be salified with an organic or inorganic acid.

Among the preferred reaction conditions of the process of the invention, the compounds of formulae II and III are reacted in a low molecular weight alkanol such as anhydrous ethanol in the presence of a base such as sodium. The saponification of the compounds of formula Ia is preferably effected with an alkali metal hydroxide such as sodium hydroxide at a temperature from room temperature to reflux.

To prepare the salts of the compounds of formula I where $R_1$ is other than hydroxy, it is preferred to react substantially stoichiometric amounts of the compound and the mineral or organic acid in an organic solvent such as ether. Where $R_1$ is hydroxy, it is also advantageous to react the metal hydroxide or nitrogen base with approximately stoichiometric proportions in an organic solvent such as ethanol.

The products of formula I wherein R is $$-\underset{\underset{CH_3}{|}}{CH}-\overset{O}{\overset{\|}{C}}-R_2$$

may occur as racemic mixtures or optically active isomers. These compounds wherein $R_2$ is —OH or —NH—$(CH_2)_n$—COOH may be resolved in the usual fashion by action of an optically active organic base such as cinchonine, cinchonidine, quinine, quinidine, brucine or α-phenylethylamine. The optically active isomers of the acids may then be esterified as indicated above.

The compounds of the invention also include the optically isomers of the formula $$\underset{\underset{CH_2-S-\underset{\underset{CH_3}{|}}{CH}-\overset{O}{\overset{\|}{C}}-R_2}{|}}{\overset{N-O}{\underset{N=C}{C}}}\quad \text{Id}$$

wherein $R_2$ has the above definition and the salts thereof which can be prepared as discussed above. Preferred optically active isomers of formula Id are 2-[S-(3-phenyl-1,2,4-oxadiazol -5-yl)-methyl]-thiopropionic acid and the ethyl esters thereof.

The novel antitussive and respiratory anti-inflammatory compositions of the invention are comprised of an effective amount of at least one compound selected from the group consisting of compounds of formula I and their non-toxic, pharmaceutically acceptable salts and an inert pharmaceutical carrier. The compositions may be in the form of tablets, dragees, gelules, capsules, granules, suppositories, syrups, aerosols and injectable solutions or suspensions prepared in the usual fashion.

The inert carrier or excipient may be those usually used such as talc, arabic gum, lactose, starch, magnesium stearate, cacao butter, aqueous or non-aqueous vehicles, fatty bodies of animal or vegetable origin, paraffinic derivatives, glycols, preservatives or diverse wetting agents, emulsifiers or dispersants.

Among the preferred compositions are those wherein R is

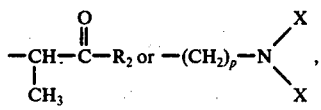

wherein $R_2$, $p$ and X have the above definitions as well as their non-toxic, pharmaceutically acceptable salts and especially those wherein R is

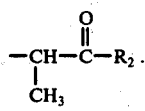

Specific preferred compounds are 3-[S-(3-phenyl-1,2,4-oxadiazol-5-yl)-methyl]-thiopropionic acid, 2-[S-(3-phenyl-1,2,4-oxadiazol-5-yl)-methyl]-thiopropionic acid, 2-[S-(3-phenyl-1,2,4-oxadiazol-5-yl)-methyl]-thiopropionylglycine and their non-toxic, pharmaceutically acceptable esters and salts and 2-[S-(3-phenyl-1,2,4-oxadiazol-5-yl)-methyl]-dimethylaminoethanethiol hydrochloride.

The compositions of the invention are useful for the treatment of coughs, acute or chronic bronchitis, treatment and prevention of bronchopulmonaries affections of infectious origin, of immunological deficiencies, of agressions of tobacco as well as the treatment and prevention of acute and chronic bronchial hypersecretions.

The novel method of the invention for inducing respiratory anti-inflammatory and peripheric antitussive activity in warm-blooded animals including humans comprises administering to warm-blooded animals an effective amount of at least one compound of formula I and their non-toxic, pharmaceutically acceptable salts. The compounds may be administered orally, rectally or parenterally and the usual effective dose is 0.02 to 5 mg/kg depending on the product and the method of administration.

The products of formula III wherein B is mercapto and R' is

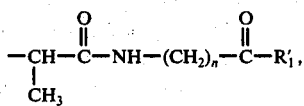

$n$ is 1 or 2 and $R_1'$ is alkoxy of 1 to 4 carbon atoms may be prepared by reacting an acid of the formula

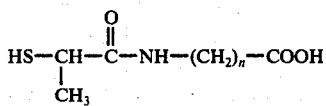

with an alcohol of the formula $R_1'$—OH.

In the following examples there are described several preferred embodiments to illustrate the invention. However, it is to be understood that the invention is not intended to be limited to the specific embodiments.

EXAMPLE 1 ethyl 3-[S-(3-phenyl-1,2,4-oxadiazol-5-yl)-methyl]-thiopropionate

A solution of 13.4 g of ethyl 3-thiopropionate in 75 ml of absolute ethanol and a solution of 19.45 g of 5-chloromethyl-3-phenyl-1,2,4-oxadiazole in 75 ml of absolute ethanol were added dropwise to a solution of 2.3 g of sodium in 75 ml of absolute ethanol and the mixture was then refluxed for 4 hours. The ethanol was distilled off to obtain 27.4 g of ethyl 3-[S-(3-phenyl-1,2,4-oxadiazol-5-yl)-methyl]-thiopropionate in the form of an oil with a boiling point of 182°–184° C at 1mm Hg.

Analysis: $C_{14}H_{16}N_2O_3S$; molecular weight = 292.3
Calculated: %C 57.51, %H 5.51, %N 9.58, %S 10.96
Found: 58.98, 5.41, 10.71, 11.89.

EXAMPLE 2

3-[S-(3-phenyl-1,2,4-oxadiazol-5-yl)-methyl]-thiopropionic acid

A mixture of 14 g of ethyl 3-[S-(3-phenyl-1,2,4-oxadiazol-5-yl)-methyl]-thiopropionate in 53.2 ml of 1N sodium hydroxide and 40 ml of water was refluxed for 2 hours and the mixture was then cooled and extracted with ether. The aqueous phase was acidified to a pH of 1–2 by addition of 2N hydrochloric acid and was extracted with ether. The ether phase was dried over magnesium sulfate and the ether was evaporated. The residue was crystallized from a 1-1 water-acetone mixture to obtain 7.4 g of 3-[S-(3-phenyl-1,2,4-oxadizol-5-yl)-methyl]-thiopropionic acid in the form of a white solid melting at 110° C.

Analysis: $C_{12}H_{12}N_2O_3S$; molecular weight = 264
Calculated: %C 54.53, %H 4.57, %N 10.59, %S 12.13.
Found: 53.96, 4.53, 10.44, 12.48.

EXAMPLE 3 ethyl 2-[S-(3-phenyl-1,2,4-oxadiazol-5-yl)-methyl]-thiopropionate

A solution of 13.4 g of ethyl thiolactate in 40 ml of absolute ethanol was added dropwise to a solution of 2.3 g of sodium in 75 ml of absolute ethanol followed by the slow addition of a solution of 19.45 g of 5-chloromethyl-3-phenyl-1,2,4-oxadiazole in 75 ml of absolute ethanol and the mixture was refluxed for 5 hours and then was filtered. The filtrate was evaporated to dryness and the residue was taken up in 100 ml of ether. The solution was washed with 75 ml of water, dried over magnesium sulfate and evaporated to dryness under reduced pressure to obtain 22 g of ethyl 2-[S-(3-phenyl-1,2,4-oxadiazol-5-yl)-methyl]-thiopropionate in the form of a clear yellow oil with a boiling point of 162°–165° C at 0.5 mm Hg.

Analysis: $C_{14}H_{16}N_2O_3S$; molecular weight = 292.36.
Calculated: %C 57.55, %H 5.51, %N 9.57, %S 10.96.
Found: 57.22, 5.51, 9.28, 10.99.

EXAMPLE 4

2-[S-(3-phenyl-1,2,4-oxadiazol-5-yl)-methyl]-thiopropionic acid

A suspension of 14.5 g of ethyl 2-[S-(3-phenyl-1,2,4-oxadiazol-5-yl)-methyl]-thiopropionate, 55 ml of N sodium hydroxide solution and 40 ml of water was refluxed for 30 minutes and was then cooled. The mixture was diluted with 50 ml of water and was extracted with ether. The aqueous phase was acidified to a pH of 2 by addition of 2N hydrochloric acid and was extracted with ether. The combined ether phases were dried over magnesium sulfate and evaporated until a thick oil formed which slowly crystallized. The product was dissolved in 50 ml of carbon tetrachloride and was crystallized to obtain 9.5 g of 2-[S-(3-phenyl-1,2,4-oxadiazol-5-yl)-methyl]-thiopropionic acid in the form of white crystals melting at 69° C. Analysis: $C_{12}H_{12}N_2O_3S$; molecular weight = 264.31 Calculated %C 54.52, %H 4.57, %N 10.58, %S 12.13. Found: 54.29, 4.61, 10.78, 12.23.

EXAMPLE 5 dimethylaminoethyl 2-[S-(3-phenyl-1,2,4-oxadiazol-5-yl)-methyl]-thiopropionate hydrochloride Gaseous hydrogen chloride was bubbled for 15 minutes into a solution of 5.34 g of dimethylaminoethanol in 100 ml of benzene and then a solution of 10.56 g of 2-[S-(3-phenyl-1,2,4-oxadiazol-5-yl)-methyl]-thiopropionic acid in 50 ml of benzene was added to the mixture at reflux. The mixture was refluxed for 5 hours while bubbling hydrogen chloride therethrough and was then cooled. The benzene was decanted and the oil was dissolved in water. The solution was made alkaline by addition of sodium carbonate and was extracted with ether. The ether extracts were dried and gaseous hydrogen chloride was bubbled therethrough to obtain 7 g of dimethylaminoethyl 2-[S-(3-phenyl-1,2,4-oxadiazol-5-yl)-methyl]-thiopropionate hydrochloride in the form of an oil which crystallized. The crystals melted at 82° C.

Analysis: $C_{16}H_{22}N_3O_3SCl$; molecular weight = 371.88 Calculated: %C 51.67, %H 5.96, %N 11.29, %S 8.62. Found: 51.42, 5.86, 11.01, 8.90.

EXAMPLE 6 potassium 2-[S-(3-phenyl-1,2,4-oxadiazol-5-yl)-methyl]-thiopropionate

A solution of 1.267 g of 2-[S-(3-phenyl-1,2,4-oxadiazol-5-yl)-methyl]-thiopropionic acid in 10 ml of 0.48N potassium ethanolate was evaporated to dryness and the residue was dried in a desiccator to obtain 1.43 g of potassium 2-[S-(3-phenyl-1,2,4-oxadiazol-5-yl)-methyl]-thiopropionate decomposing at 90° C.

Analysis: $C_{12}H_{11}N_2O_3SK$; molecular weight = 302.39 Calculated: %C 47.66, %H 3.66, %N 9.26, %S 10.60. Found: 47.92, 3.82, 9.13, 10.20.

EXAMPLE 7

Lysine salt of 2-[S-(3-phenyl-1,2,4-oxadiazol-5-yl)-methyl]-thiopropionic acid

A solution of 2.5 g of L-lysine (49%) in 5 ml of ethanol was added to a mixture of 2.64 g of 2-[S-(3-phenyl-1,2,4-oxadiazol-5-yl)-methyl]-thiopropionic acid in 15 ml of ethanol and the mixture was stirred for 15 minutes and then was evaporated to dryness. The residue was taken up 3 times with anhydrous benzene and was then evaporated to dryness under reduced pressure. The residue was washed with acetone and then dried to obtain 3.5 g of the lysine salt of 2-[S-(3-phenyl-1,2,4-oxadiazol-5-yl)-methyl]-thiopropionic acid in the form of hygroscopic white crystals melting towards 100° C.

Analysis: $C_{18}H_{26}N_4O_5S$; molecular weight = 410.49. Calculated: %C 52.67, %H 6.38, %N 13.65, %S 7.81. Found: 52.62, 6.44, 13.58, 7.92.

EXAMPLE 8 triethanolamine 2-[S-(3-phenyl-1,2,4-oxadiazol-5-yl)-methyl]-thiopropionate

A mixture of 2.64 g of 2-[S-(3-phenyl-1,2,4-oxadiazol-5-yl)-methyl]-thiopropionic acid, 1.17 g of triethanolamine and 20 ml of ethanol was stirred for 15 minutes and 200 ml of ether were added to obtain 3 g of the triethanolamine salt of the said acid in the form of an oil which crystallized in the cold.

Analysis: $C_{18}H_{27}N_3O_6S$; molecular weight = 413.49. Calculated: %C 52.28, %H 6.58, %N 10.16, %S 7.75. Found: 52.09, 6.46, 10.42, 8.02.

EXAMPLE 9 ethyl 2-[S-(3-phenyl-1,2,4-oxadiazol-5-yl)-methyl]-thiopropionylglycinate

STEP A: ethyl 2-mercapto propionylglycinate

Nitrogen was bubbled through a suspension of 50 g of 2-mercapto propionylglycinate in 100 ml of absolute ethanol for 30 minutes and then gaseous hydrogen chloride was bubbled therethrough with stirring for one hour. The mixture stood overnight under a hydrogen chloride atmosphere and then the ethanol was evaporated. The residual oil was dissolved in 150 ml of ether and the ether solution was washed with water, dried over magnesium sulfate and evaporated to dryness to obtain 52 g of ethyl 2-mercapto propionylglycinate in the form of a colorless oil which was used as is for the next step.

STEP B: ethyl 2-[S-(3-phenyl-1,2,4-oxadiazol-5-yl)-methyl]-thiopropionylglycinate A solution of 19.1 g of ethyl 2-mercapto propionylglycinate in 100 ml of absolute ethanol was added dropwise to a solution of 2.3 g of sodium in 75 ml of absolute ethanol and then a solution of 19.45 g of 5-chloromethyl-3-phenyl-1,2,4-oxadiazol in 100 ml of absolute ethanol was slowly added thereto. The mixture was refluxed for 4 hours and was cooled and evaporated to dryness. The residue was dissolved in 500 ml of methylene chloride and the solution was washed with water, dried over magnesium sulfate and evaporated to dryness to obtain crystals which were taken up in ether to obtain 23 g of ethyl 2-[S-(3-phenyl-1,2,4-oxadiazol-5-yl)-methyl]-thiopropionylglycinate in the form of white crystals melting at 96° C.

Analysis: $C_{16}H_{19}N_3O_4S$; molecular weight = 349. Calculated: %C 55, %H 5.48, %N 12.05, %S 9.15. Found: 55.18, 5.45, 12.04, 9.00.

EXAMPLE 10

2-[S-(3-phenyl-1,2,4-oxadiazol-5-yl)-methyl]-thiopropionylglycine

A mixture of 10.5 g of ethyl 2-[S-(3-phenyl-1,2,4-oxadiazol-5-yl)-methyl]-thiopropionylglycinate, 45 ml of 1N sodium hydroxide and 50 ml of water was stirred and heated just high enough to obtain a homogenous medium and then was cooled and extracted with ether. The aqueous phase was acidified to a pH of 2 by addition of 2N hydrochloric acid and the oil obtained was extracted with ether. The ether phase was dried over magnesium sulfate and the ether was evaporated. The residue was crystallized from a 1-1 hexane-ethyl acetate mixture to obtain 8.5 g of 2-[S-(3-phenyl-1,2,4-oxadiazol-5-yl)-methyl]-thiopropionylglycine in the form of a white solid melting at 112° C.

Analysis: $C_{14}H_{15}N_3O_4S$; molecular weight = 321.2. Calculated: %C 52.5, %H 4.70, %N 13.05, %S 9.95. Found: 52.21, 4.91, 12.89, 9.94.

EXAMPLE 11 dimethylaminoethyl 2-[S-(3-phenyl-1,2,4-oxadiazol-5-yl)-methyl]-thiopropionylglycinate A mixture of 32.1 g of 2-[S-(3-phenyl-1,2,4-oxadiazol-5-yl)-methyl]-thiopropionylglycine, 13.5 g of dimethylaminoethanol and 250 ml of benzene was refluxed for 3 hours while bubbling dry gaseous hydrogen chloride therethrough and the mixture was cooled. The benzene was decanted and the residual oil was dissolved in a minimum of water. The solution was added to methylene chloride and the mixture was adjusted to a pH of 8 by addition of sodium carbonate. The organic phase was washed with water, dried over magnesium sulfate and evaporated to dryness. The residue crystallized and was washed with hexane to obtain 19 g of dimethylaminoethyl 2-[S-(3-phenyl-1,2,4-oxadiazol-5-yl)-methyl]-thiopropionylglycinate in the form of a white solid melting at 50°-52° C.

Analysis: $C_{18}H_{24}N_4O_4S$; molecular weight = 392.481. Calculated: %N 14.30, %S 8.16. Found: 14.25, 8.17.

EXAMPLE 12 diethylaminoethyl 2-[S-(3-phenyl-1,2,4-oxadiazol-5-yl)-methyl]-thiopropionylglycinate A mixture of 7.02 g of diethylaminoethanol in 100 ml of anhydrous benzene was refluxed while bubbling dry gaseous hydrogen chloride therethrough and then a suspension of 12.8 g of 2-[S-(3-phenyl-1,2,4-oxadiazol-5-yl)-methyl]-thiopropylglycine in 100 ml of anhydrous benzene were added thereto. Reflux with hydrogen chloride bubbling was continued for 3½ hours and the mixture was cooled and the benzene decanted. The residual oil was dissolved in a minimum of water and 50 ml of a 10% sodium carbonate solution were added. The mixture was extracted with methylene chloride and the organic phase was washed with water, dried over magnesium sulfate and evaporated to dryness to obtain 8 g of diethylaminoethyl 2-[S-(3-phenyl-1,2,4-oxadiazol-5-yl)-methyl]-thiopropionylglycinate in the form of an oil.

Analysis: $C_{20}H_{28}N_4O_4S$; molecular weight = 420.535. Calculated: %C 57.1, %H 6.71, %N 13.07, %S 7.62. Found: 56.63, 6.91, 13.01, 7.65.

EXAMPLE 13 potassium 2-[S-(3-phenyl-1,2,4-oxadiazol-5-yl)-methyl]-thiopropionylglycinate

A solution of 1.54 g of the acid of Example 10 in 10 ml of 0.48N potassium ethanolate was evaporated to dryness and the product was dried in a desiccator to obtain 1.72 g of potassium 2-[S-(3-phenyl-1,2,4-oxadiazol-5-yl)-methyl]-thiopropionylglycinate which decomposed at 95° C.

Analysis: $C_{14}H_{14}N_3O_4SK$; molecular weight = 359.45 Calculated: %C 46.78, %H 3.92, %N 11.69, %S 8.92. Found: 46.48, 4.06, 11.75, 8.46.

EXAMPLE 14

L-lysine salt of 2-[S-(3-phenyl-1,2,4-oxadiazol-5-yl)-methyl]-thiopropionylglycine 7 g of L-lysine (49%) in 5 ml of water were added to a mixture of 8 g of 2-[S-(3-phenyl-1,2,4-oxadiazol-5-yl)-methyl]-thiopropionylglycine in 15 ml of water and the mixture was heated at 40° C with stirring for 20 minutes. After cooling, 200 ml of acetone were added and the mixture was cooled and vacuum filtered. The solid product was washed with acetone and then with ethanol and dried to obtain 10 g of the L-lysine salt of 2-[S-(3-phenyl-1,2,4-oxadiazol-5-yl)-methyl]-thiopropionylglycine in the form of white crystals melting at 164°-166° C.

Analysis: $C_{20}H_{29}N_5O_6S.1H_2O$; molecular weight = 485.55 Calculated: %C 49.47, %H 6.43, %N 14.42, %S 6.60. Found: 50.36, 6.48, 14.38, 6.27.

EXAMPLE 15 triethanolamine 2-[S-(3-phenyl-1,2,4-oxadiazol-5-yl)-methyl]-thiopropionylglycinate A mixture of 4.8 g of the acid of Example 10, 2 g of triethanolamine and 15 ml of water stood for 15 minutes and was then evaporated to dryness. The residue was taken up in ethanol and 200 ml of ether were added to obtain 5.7 g of triethanolamine 2-[S-(3-phenyl-1,2,4-oxadiazol-5-yl)-methyl]-thiopropionylglycinate in the form of an oil which crystallized and melted at 62°-64° C.

Analysis: $C_{20}H_{30}N_4O_7S$; molecular weight = 470.54 Calculated: %C 51.05, %H 6.42, %N 11.90, %S 6.81. Found: 51.35, 6.44, 11.80, 6.81.

EXAMPLE 16

2-[S-(3-phenyl-1,2,4-oxadiazol-5-yl)-methyl]-thiodimethylaminoethane .HCl

A mixture of 14.15 g of dimethylamino-ethanethiol in 500 ml of absolute ethanol was slowly added to a solution of 4.6 g of sodium in 190 ml of absolute ethanol and the mixture was then allowed to stand for 15 minutes. A solution of 19.45 g of 5-chloromethyl-3-phenyl-1,2,4-oxadiazole in 200 ml of absolute ethanol was added dropwise thereto and the mixture was refluxed for 3 hours and then was cooled. The mixture was filtered and the filtrate was evaporated to dryness. The residue was taken up in a minimum of ether and the solution was washed with sodium bicarbonate solution, then with water and dried over magnesium sulfate. Gaseous hydrogen chloride was bubbled through the solution and after crystallization, the mixture was filtered. The solid was taken up in methanol and ether addition caused a precipitation to obtain 18 g of 2-[S-(3-phenyl-1,2,4-oxadiazol-5-yl)-methyl]-thiodimethylaminoethane hydrochloride in the form of a white solid melting at 134° C.

Analysis: $C_{13}H_{17}N_3O$ S.HCl; molecular weight = 300. Calculated: %C 52.07, %H 6.05, %N 14.01, %S 10.69. Found: 52.07, 5.99, 14.13, 10.95.

EXAMPLE 17 resolution of racemic 2-[S-(3-phenyl-1,2,4-oxadiazol-5-yl)-methyl]-thiopropionic acid A mixture of 26.4 g of racemic 2-[S-(3-phenyl-1,2,4-oxadiazol-5-yl)-methyl]-thiopropionic acid, 29.4 g of cinchonine and 100 ml of methanol was refluxed for 3 hours and after cooling, the mixture was evaporated to dryness. The residue was dissolved in 100 ml of boiling acetone and the solution was allowed to stand for 48 hours. The precipitate formed was recovered by vacuum filtration and was washed with acetone.

The filtrate was evaporated under reduced pressure and the oily residue was taken up in 10 ml of ethanol and 75 ml of N hydrochloric acid were added thereto. The mixture was extracted with ether and the ether extracts were washed with N hydrochloric acid, with water, dried and evaporated to dryness. The residue was crystallized from carbon tetrachloride to obtain 9 g of crystals of 2-[S-(3-phenyl-1,2,4-oxadiazol-5-yl)-methyl]-thiopropionic acid with a specific rotation of $[\alpha]_D^{20} = +4.7°$ (chloroform).

The precipiate obtained above was dissolved in 75 ml of boiling acetone and the mixture was allowed to stand for 24 hours at 20° C. The precipitate was recovered by vacuum filtration and was washed with acetone and the filtrate was saved. The precipitate was treated with N hydrochloric acid as previously to obtain 8 g of crystals of 2-[S-(3-phenyl-1,2,4-oxadiazol-5-yl)-methyl]-thiopropionic acid with a specific rotation $[\alpha]_D^{20} = -10°$ (chloroform). The filtrate was evaporated to dryness and the residue was treated with hydrochloric acid as before to obtain an additional 4 g of crystals with a specific rotation $[\alpha]_D^{20} = +4.7°$ (chloroform).

EXAMPLE 18 ethyl esters of resolved 2-[S-(3-phenyl-1,2,4-oxadiazol-5-yl)-methyl]-thiopropionic acid A. Anhydrous hydrogen chloride was bubbled through 50 ml of ethanol for 15 minutes and after cooling the solution, a mixture of 1 g of the laevo-rotatory acid of Example 17 in 20 ml of the ethanolic hydrogen chloride solution was stirred at room temperature for 16 hours and the mixture was then evaporated to dryness. The residue was taken up in ether and the solution was washed with water and sodium bicarbonate solution, was dried and evaporated to dryness to obtain the ethyl ester of the laevo-rotatory form of 2-/S-(3-phenyl-1,2,4-oxadiazol-5-yl)-methyl/-thiopropionic acid with a specific rotation $[\alpha]_D^{20} = -10.9°$ (chloroform).

B. Using the same procedure, 0.5 g of the dextro rotatory form of the said acid was esterified to obtain the ethyl ester of the dextro rotatory form of 2-/S-(3-phenyl-1,2,4-oxadiazol-5-yl)-methyl/-thiopropionic acid with a specific rotation $[\alpha]_D^{20} = +6.25°$ (chloroform).

EXAMPLE 19

Tablets were prepared containing 75 mg of ethyl 2-[S-(3-phenyl-1,2,4-oxadiazol-5-yl)-methyl]-thiopropionylglycinate and sufficient excipient of lactose, starch, talc and magnesium stearate for a final tablet weight of 200 mg.

A syrup was prepared from 2 g of lysine salt of 2-[S-(3-phenyl-1,2,4-oxadiazol-5-yl)-methyl]-thiopropionylgylcine and sufficient sweetened and aromatized excipient to obtain 100 ml of solution.

An aerosol for inhalation containing for each dose 5 mg of the active ingredient was prepared and consisted of 5 mg of 2-[S-(3-phenyl-1,2,4-oxadiazol-5-yl)-methyl]-dimethylaminoethanethiol hydrochloride, 0.07 mg of an emulsifier and 50 mg of a propulsion agent.

PHARMACOLOGICAL DATA

Antitussive — Respiratory Anti-inflammatory Activity

This activity of the compounds of the invention was determined with guinea pigs against experimental coughing provoked by citric acid using the method of Winter et al modified by Boissier [1959 Congress Threapeut. Strasbourg, p. 275–295 (Doin)]. The test consists of administrating over 4 minutes an aerosol spray of 40% citric acid to male guinea pigs weighing 300 to 400 g 24 hours before treatment with the test product. The animals received orally a dose of 60 mg/kg of the test compound one hour before another aerosol spray of citric acid. The respiratory anti-inflammatory-antitussive activity was determined by the number of coughs before and after treatment and the results of Table I are expressed as the percentage of protection against the irritative cough of citric acid.

TABLE I

| Product of Examples | % of Protection |
|---|---|
| 1 | 40 |
| 2 | 40 |
| 3 | 85 |
| 4 | 70 |
| 5 | 15 |
| 7 | 20 |
| 8 | 45 |
| 9 | 90 |
| 10 | 80 |
| 11 | 15 |
| 12 | 35 |
| 14 | 65 |
| 15 | 50 |
| 16 | 65 |

The results of Table I show that all the compounds possess respiratory anti-inflammatory-antitussive activity with the products of Examples 3,4,9,10,14 and 16 possessing a remarkable activity.

Acute toxicity

The acute toxicity was determined on mice after oral administrations of increasing doses of the test compounds and the number of dead mice after 8 days was determined. The lethal dose 0 (DL 0) which was the maximum dose of the product without killing any animals was determined and the results are reported in Table II.

TABLE II

| Product of Examples | D.L. 0 in mg/Kg | Example No. | D.L. 0 in mg/Kg |
|---|---|---|---|
| 1 | ≧ 240 | 9 | ≧ 1 600 |
| 2 | ≧ 240 | 10 | ≧ 1 600 |
| 3 | ≧ 240 | 11 | ≧ 240 |

TABLE II-continued

| Product of Examples | D.L. 0 in mg/Kg | Example No. | D.L. 0 in mg/Kg |
|---|---|---|---|
| 4 | ≧ 240 | 12 | ≧ 240 |
| 5 | ≧ 240 | 14 | ≧ 240 |
| 7 | ≧ 240 | 15 | ≧ 240 |
| 8 | ≧ 240 | 16 | ≧ 240 |

Various modifications of the products and methods of the invention may be made without departing from the spirit or scope thereof and it should be understood that the invention is intended to be limited only as defined in the appended claims.

We claim:

1. A compound selected from the group consisting of a compound of the formula

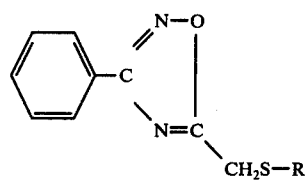

wherein R is selected from the group consisting of —(CH$_2$)$_m$—COR$_1$,

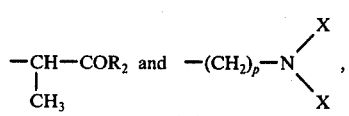

$m$ is 2,3 or 4, R$_1$ is selected from the group consisting of hydroxy, alkoxy of 1 to 4 carbon atoms and

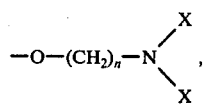

$n$ is 1 or 2, X is selected from the group consisting of hydrogen and alkyl of 1 to 4 carbon atoms, R$_2$ is selected from the group consisting of hydroxy, alkoxy of 1 to 4 carbon atoms,

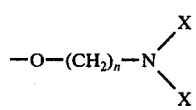

and —NH—(CH$_2$)$_n$—COR$_1$ and $p$ is 1,2,3 or 4 and the non-toxic, pharmaceutically acceptable salts thereof.

2. A compound of claim 1 wherein R is selected from the group consisting of

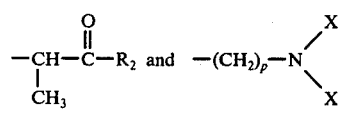

wherein R$_2$, X and $p$ have the definitions of claim 1.

3. A compound of claim 1 wherein R is

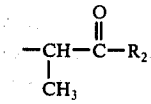

wherein R$_2$ has the definition of claim 1.

4. A compound of claim 1 selected from the group consisting of 3-[S-(3-phenyl-1,2,4-oxadiazol-5-yl)-methyl]-thiopropionic acid and its alkyl esters of 1 to 4 carbon atoms.

5. A compound of claim 1 selected from the group consisting of 2-[S-(3-phenyl-1,2,4-oxadiazol-5-yl)-methyl]-thiopropionic acid and its alkyl esters of 1 to 4 carbon atoms.

6. A compound of claim 1 which is ethyl 2-[S-(3-phenyl-1,2,4-oxadiazol-5-yl)-methyl]-thiopropionate.

7. A compound of claim 1 selected from the group consisting of 2-[S-(3-phenyl-1,2,4-oxadiazol-5 -yl)-methyl]-thiopropionylglycine and its alkyl esters of 1 to 4 carbon atoms.

8. A compound of claim 7 which is the ethyl ester.

9. A compound of claim 1 which is 2-[S-(3-phenyl-1,2,4-oxadiazol-5-yl)-methyl]-dimethylaminoethanethiol hydrochloride.

10. An optically active isomer of the product of the formula

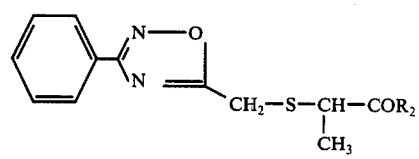

wherein R$_2$ is as defined in claim 1 and its non-toxic, pharmaceutically acceptable salts.

11. An optically active isomer of 2-[S-(3-phenyl-1,2,4-oxadiazol-5-yl)-methyl]-thiopropionic acid and its ethyl ester and its non-toxic, pharmaceutically acceptable salts.

12. An antitussive and respiratory anti-inflammatory composition comprising an effective amount of a compound of claim 1 and an inert pharmaceutical carrier.

13. The composition of claim 12 wherein R is selected from the group consisting of

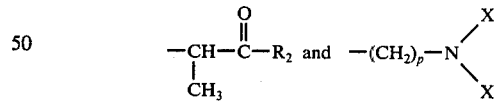

wherein R$_2$, $p$ and X have the definitions of claim 1.

14. A method of inducing respiratory anti-inflammatory and peripheric antitussive activity in warm-blooded animals comprising administering to warm-blooded animals an anti-inflammatory and antitussively effective amount of a compound of claim 1.

15. The method of claim 14 wherein R is selected from the group consisting of

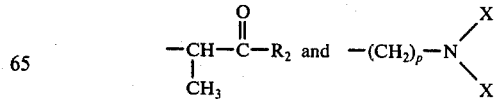

wherein X, $p$ and R$_2$ have the definition of claim 1.

16. The method of claim 14 wherein 3-[S-(3-phenyl-1,2,4-oxadiazol-5-yl)-methyl]-thiopropionic acid and its alkyl esters of 1 to 4 carbon atoms are used.

17. The method of claim 14 wherein 2-[S-(3-phenyl-1,2,4-oxadiazol-5-yl)-methyl]-thiopropionic acid and its alkyl esters of 1 to 4 carbon atoms are used.

18. The method of claim 14 wherein ethyl 2-[S-(3-phenyl-1,2,4-oxadiazol-5-yl)-methyl]-thiopropionate is used.

19. The method of claim 14 wherein 2-[S-(3-phenyl-1,2,4-oxadiazol-5-yl)-methyl]-thiopropionylglycine and its alkyl esters of 1 to 4 carbon atoms are used.

20. The method of claim 19 wherein the ethyl ester is used.

21. The method of claim 14 wherein 2-[S-(3-phenyl-1,2,4-oxadiazol-5-yl)-methyl]-dimethylaminoethanethiol hydrochloride is used.

22. The method of claim 14 wherein the optically active isomers of the products of the formula

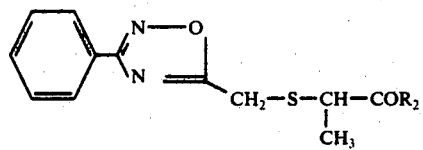

and their non-toxic, pharmaceutically acceptable salts are used.

23. The method of claim 14 wherein the optically active isomers of 2-[S-(3-phenyl-1,2,4-oxadiazol-5-yl)-methyl]-thiopropionic acid and their ethyl esters, as well as the non-toxic, pharmaceutically acceptable salts of these products are used.

* * * * *